US006548304B2

(12) United States Patent
Collins

(10) Patent No.: US 6,548,304 B2
(45) Date of Patent: Apr. 15, 2003

(54) METHOD AND APPARATUS FOR RAPID FAT CONTENT DETERMINATION

(75) Inventor: Michael J. Collins, Charlotte, NC (US)

(73) Assignee: CEM Corporation, Matthew, NC (US)

(*) Notice: Subject to any disclaimer, the term of this patent is extended or adjusted under 35 U.S.C. 154(b) by 0 days.

(21) Appl. No.: 10/108,522

(22) Filed: Mar. 28, 2002

(65) Prior Publication Data

US 2002/0146833 A1 Oct. 10, 2002

Related U.S. Application Data

(63) Continuation of application No. 09/603,487, filed on Jun. 23, 2000.

(51) Int. Cl.[7] .............................................. G01N 33/06
(52) U.S. Cl. ........................ 436/23; 436/173; 436/174; 436/176
(58) Field of Search ..................... 436/22, 23, 71, 436/173, 174, 176; 422/68.1, 74, 78

(56) References Cited

U.S. PATENT DOCUMENTS

| 3,691,455 A | 9/1972 | Moisio et al. |
| 3,966,973 A | 6/1976 | Henry et al. |
| 3,971,434 A | 7/1976 | Martin, Jr. et al. |
| 4,554,132 A | * 11/1985 | Collins ........................ 422/78 |
| 4,566,312 A | 1/1986 | Collins et al. |
| 4,651,285 A | 3/1987 | Collins et al. |
| 4,681,996 A | 7/1987 | Collins et al. |
| H000383 H | 12/1987 | Skaritka |
| 4,753,889 A | 6/1988 | Collins |
| 4,785,245 A | 11/1988 | Lew et al. |
| 5,079,505 A | 1/1992 | Deimling et al. |
| 5,144,235 A | 9/1992 | Glover et al. |
| 5,187,439 A | 2/1993 | Jensen et al. |
| 5,225,781 A | 7/1993 | Glover et al. |

(List continued on next page.)

FOREIGN PATENT DOCUMENTS

| EP | 0038254 | 10/1981 |
| EP | 0340037 | 11/1989 |
| GB | 2261072 | 5/1993 |
| WO | WO99/54035 | 10/1999 |
| WO | WO99/54751 | 10/1999 |
| WO | WO00/16067 | 3/2000 |

OTHER PUBLICATIONS

Eads, Thomas M. and Croasmun, William R.; NMR applications to fats and oils; JAOCS, Jan. 1988, vol. 65, No. 1.
Renou, J.P., Briguet, A., Gatellier, Ph., and Kopp, J.; Technical note: Determination of fat and water ratios in meat products by high resolution NMR at 19.6MHz; International Journal of Food Science and Technology, 1987, vol. 22, pp. 169–172.
Casey, John C. and Miles, Christopher A.; Determination of the Fat Content of meat Using Nuclear Magnetic Resonance; J. Sci. Fd Agric., 1974, pp. 1155–1161.

(List continued on next page.)

Primary Examiner—Jill Warden
Assistant Examiner—Yelena Gakh
(74) Attorney, Agent, or Firm—Summa & Allan, P.A.

(57) ABSTRACT

A method and apparatus for rapidly and accurately determining the fat and oil content of a sample using microwave drying and NMR analysis is disclosed. The method and apparatus incorporate a low mass, porous, hydrophilic and lipophilic sample pad that ensures that the entire sample is subjected to NMR analysis. The method and apparatus according to the invention are suitable for rapidly determining the fat and oil content of samples collected during a production process and for process or quality control.

8 Claims, 7 Drawing Sheets

U.S. PATENT DOCUMENTS

| | | | |
|---|---|---|---|
| 5,289,124 A | * | 2/1994 | Jerosch-Herold et al. ... 324/303 |
| 5,328,577 A | | 7/1994 | Murphy |
| 5,378,878 A | | 1/1995 | Revesz |
| 5,602,477 A | | 2/1997 | McCarthy et al. |
| 5,660,865 A | | 8/1997 | Pederson et al. |
| 5,770,251 A | | 6/1998 | Finucane et al. |
| 5,909,119 A | | 6/1999 | Zhang et al. |
| 6,005,389 A | | 12/1999 | Prammer |

OTHER PUBLICATIONS

Gribnau, M.C.M., Determination of solid/liquid ratios of fats and oils by low–resolution pulsed NMR; Tends in Food Science & Technology, Aug./Sep. 1992.

"History of Teflon" @http:/www.dupont.com/telfon/newsroom/history.html.

* cited by examiner

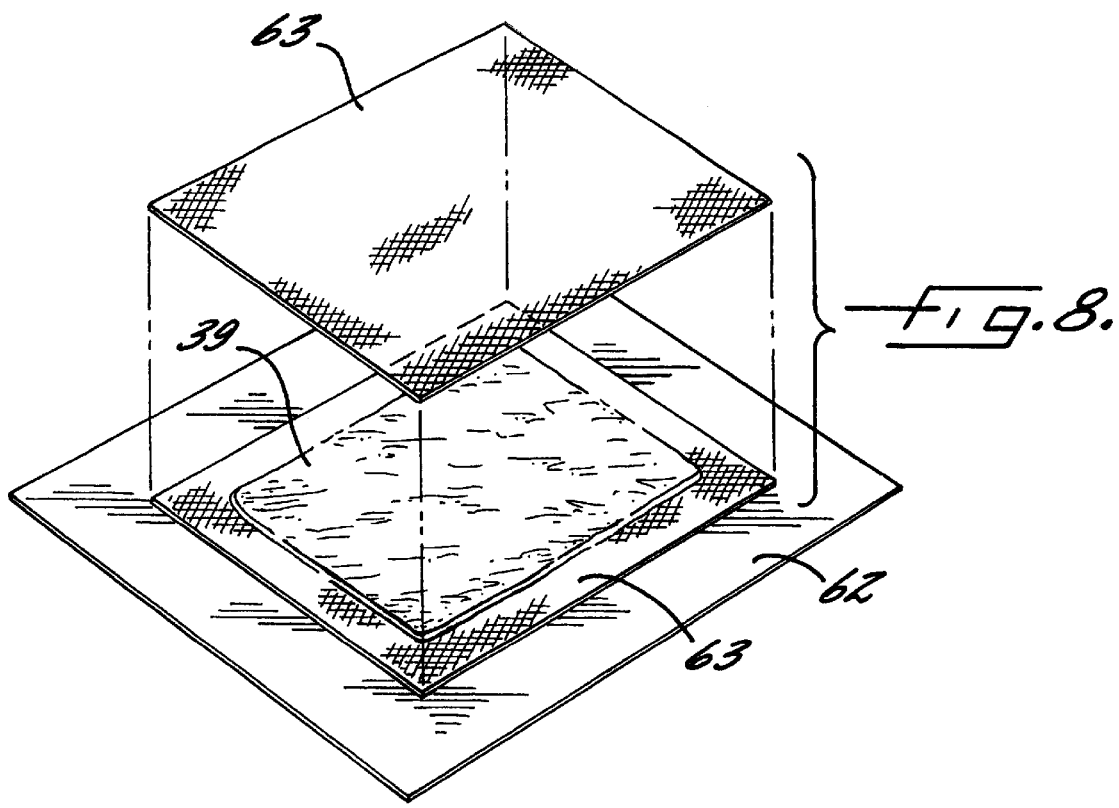
Fig. 8.
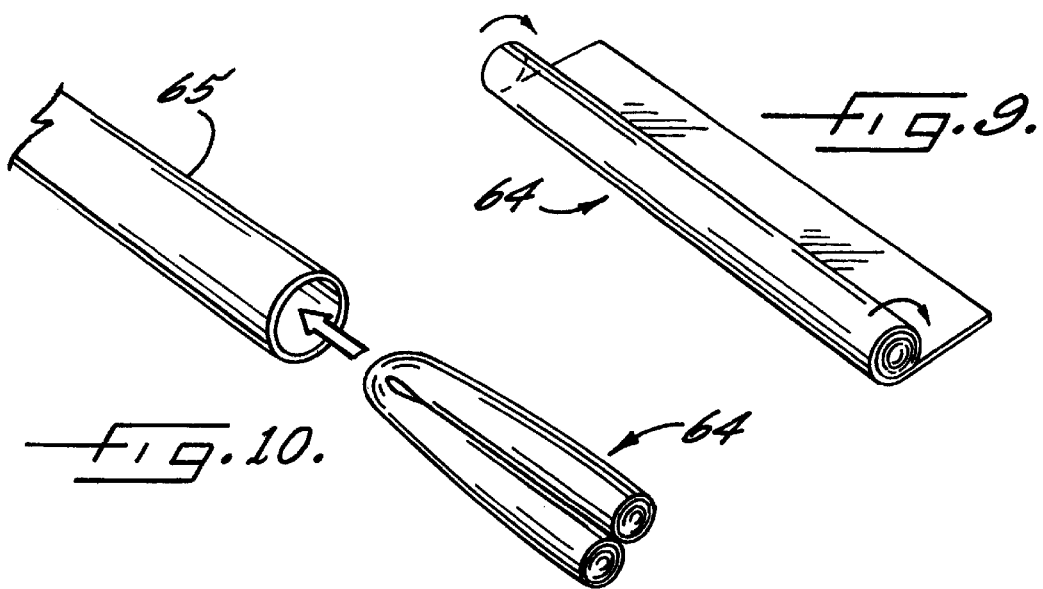
Fig. 9.
Fig. 10.

METHOD AND APPARATUS FOR RAPID FAT CONTENT DETERMINATION

This is a continuation of Ser. No. 09/603,487 filed Jun. 23, 2000.

FIELD OF THE INVENTION

The present invention relates to chemical analysis using microwave assisted nuclear magnetic resonance ("NMR"). In particular the invention relates to determining the moisture and fat and oil content of samples using NMR and microwave radiation.

BACKGROUND OF THE INVENTION

The present invention relates to chemical analysis of foodstuffs or other materials for which it is advantageous to know the moisture and fat (and oil) content of the material. For example, commercial production of processed foods such as hot dogs and cheese requires close control of fat and oil content. Variation in fat and oil content during the production process is detrimental to product quality and can adversely affect production economics. From a more positive standpoint, the fat content of a sample also provides useful information about food products such as texture, heat resistance, mouth feel, and flavor release. Additionally, many foods are subject to various statutory and regulatory labeling and content requirements with respect to the fats and oils they contain. Information about fat and oil content is often valuable or necessary in controlling various food processing techniques.

Those skilled in the art know that there is little chemical difference between fats and oils, the primary distinction being that fats are solid at room temperature and oils are liquid. Accordingly, the terms "fat" and "oil" may be used interchangeably herein.

Traditional methods for determining the moisture and fat content of foodstuffs include extensive drying and solvent based chemical extractions. These traditional methods are time consuming. The time lag inherent in the most widely used testing methods prevents production processes from operating at optimal efficiency. Furthermore, many methods require solvents that are expensive, often hazardous, and pose disposal problems. Accordingly, scientists have sought alternative means for determining fat and oil content in samples.

Since the late 1960's scientists have proposed using NMR as an alternative means of determining the fat and moisture content of foodstuffs. NMR analysis is essentially a spectroscopic method that measures a phenomenon that occurs when the nuclei of certain atoms are placed in a static magnetic field and then exposed to a second oscillating electromagnetic field. In very simplistic terms, during NMR analysis a substance is placed in a magnetic field that affects the "spin" of the atomic nuclei of certain isotopes of elements. The nuclei orient themselves in a specific way in response to the magnetic field. If a second radio frequency (RF) magnetic field (e.g., radio wave) is passed over the nuclei, the protons in the nuclei will be made to reorient or "flip" when the RF field reaches a specific frequency. When the RF field is turned off, the nuclei "flip" back releasing energy that provides data on the molecular structure of the substance. This back-and-forth orienting of nuclei is known as resonance.

NMR resonance occurs at different frequencies for different materials. For liquids, the frequency band for NMR resonance is relatively narrow. For solids, the frequency band is broader. This distinction in NMR resonance makes it possible to distinguish the protons of liquid from those of solid constituents of the sample. In this manner the percentage of liquid and solid in a sample may be determined.

In another type of NMR, referred to as "pulsed" NMR, a sample is exposed to a pulse of radio frequency ("RF") energy that magnetizes ("flips") the proton nuclear magnetic moments in the sample. Following the pulse, the protons return to their initial states ("relaxation"), but do so over a characteristic period of time (relaxation time) that reflects the chemical surroundings of the proton, and thus the composition of the sample. A representative (although not limiting) discussion of pulsed NMR is set forth in published U.K. Patent Application GB2261072A.

Furthermore, under proper circumstances, NMR can distinguish not only between liquids and solids, but also between chemical compounds. Theoretically, in abstract circumstances, all protons should resonate at the same frequency or relax over the same time period. Surrounding electrons, however, interfere with the magnetic field acting upon a given proton, and thus each proton will resonate at a slightly different frequency, or relax over a different time period, depending upon the electron density around it. As a result, different compounds (and different functional groups within compounds) have different resonance frequencies and different relaxation times. These differences are typically represented as graphical peaks along a spectrum that plots resonance frequency or relaxation time, depending upon the type of NMR being used.

As mentioned previously, NMR has long held promise as an alternative to solvent extraction for quantitatively determining the components of a sample. Efficiently utilizing NMR in this regard, however, has proven difficult. This difficulty is especially prevalent in determining the fat and oil content of foodstuff samples.

For example, NMR resonance occurs over a narrow band for liquids and this narrow window of NMR resonance is used to easily distinguish liquids from solids. Traditional fat and oil analysis takes advantage of this by melting all the fat and oil in a sample prior to NMR analysis. Because many foods have a relatively high moisture content, and because high moisture content usually makes NMR analysis unfeasible, food samples typically must be thoroughly dried prior to NMR analysis.

After the sample is dried, the sample is usually heated until all the fat and oil present in the sample is assumed to have melted, with the further assumption that the only liquid remaining in the sample is fat. Melting the fat and oil also means that a portion of the fat and oil may drain from the sample. As a result, when the sample is removed from the oven and prepared for NMR analysis, the sample no longer contains the same amount of fat and oil as did the original sample. As a further disadvantage, if aggressive heating techniques, such as very hot convection ovens or conventional microwave ovens, are used to speed drying of the sample, the chemical structure of the sample may be altered (e.g., meat is cooked) which may alter the NMR results and provide a less accurate-or even highly inaccurate-analysis.

One proposed method for avoiding the problems associated with conventional drying techniques is to chemically remove the water from the sample prior to conducting a NMR analysis. UK Patent Application GB 2,261,072 proposes to chemically remove the water from the sample through the addition of a drying agent such as calcium carbide or calcium oxide. The addition of these drying agents, however, must be based upon expected moisture content. Accordingly, errors in the addition of the drying agent are unavoidable. Such errors affect the weight of the sample and possibly the NMR analysis (if moisture remains in the sample) thereby providing inaccurate results for fat and oil content.

In short, current methods for determining fat and oil content possess a high degree of statistical uncertainty or are unsuitable for continuous production processes. Therefore, a need exists for a method and apparatus for determining the fat and oil content of samples that does not possess the inherent inaccuracy of known methods. Preferably this new method and apparatus will rapidly and accurately determine the fat and oil content of a sample thereby providing a more efficient overall production process.

OBJECT AND SUMMARY OF THE INVENTION

Therefore, it is an object of the invention to provide a method and apparatus for rapidly and accurately determining the moisture content and the fat and oil content of a sample that also contains moisture in amounts that would otherwise preclude a NMR determination of the fat and oil content.

The invention meets this object with a method of rapidly and accurately determining the fat and oil content of a sample that also contains moisture in amounts that would otherwise preclude NMR determination of the fat and oil content. The method comprises weighing the sample and drying the sample by subjecting the sample to electromagnetic radiation in the microwave frequencies. After the sample is dried the entire sample, along with the pad supporting the sample, is transferred to an NMR analyzer. The NMR analyzer identifies the response of protons in the sample that are associated with fats and oils. The NMR response of the sample is then compared to the NMR response of similar samples having a known fat and oil content. By making this comparison in conjunction with analysis of weight data collected before, during and after the drying step, a quantitative determination of the fat and oil content in the sample may be achieved.

The invention also meets this object with an apparatus for rapidly and accurately determining the fat and oil content of a sample that also contains moisture in amounts that would otherwise preclude NMR determination of the fat and oil content. The apparatus according to the invention comprises a sample pad for receiving a sample containing fat and oil and a source of microwave radiation for drying the sample. The source of microwave radiation is in wave communication with a cavity for receiving the sample and sample pad. A balance is situated with at least its pan within the cavity for weighing the sample and sample pad before, during and after drying of the sample. The apparatus further comprises a NMR analyzer for determining the NMR response of the components of the sample. In preferred embodiments, the NMR analyzer and the microwave device are situated close enough to one another to prevent a significant temperature drop in the sample during transfer of the sample from the microwave cavity to the NMR analyzer.

The foregoing and other objects and advantages of the invention and the manner in which the same are accomplished will become clearer based on the followed detailed description taken in conjunction with the accompanying drawings in which:

BRIEF DESCRIPTION OF THE DRAWINGS

FIGS. 8–10 are perspective views illustrate another aspect of the method and apparatus of the invention.

DETAILED DESCRIPTION

Figure 1A:
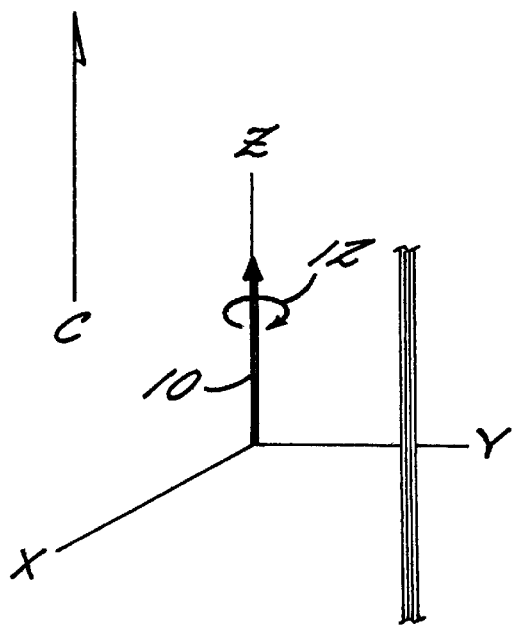
FIGS. 1a–1d are progressional diagrammatic representations of the motion of a nuclear magnetic moment producing a NMR emission.
Figure 1B:
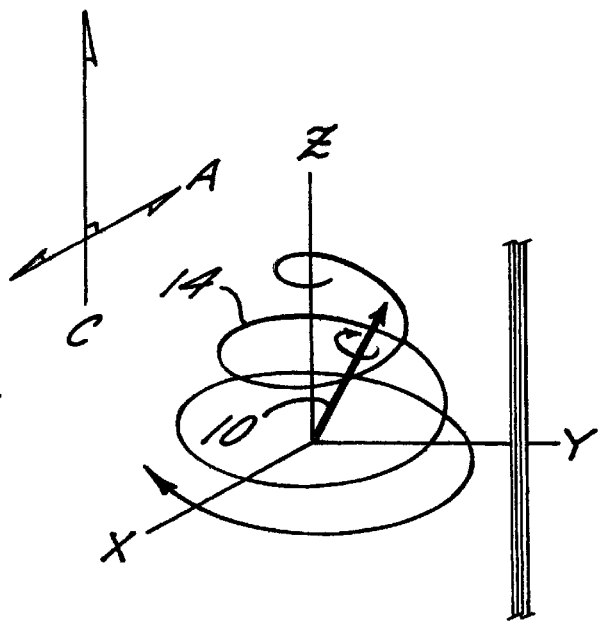
Figure 1C:
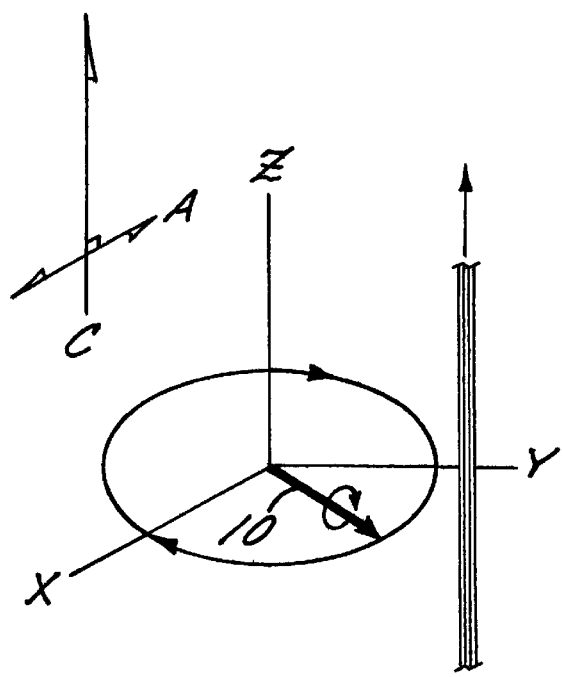
Figure 1D:
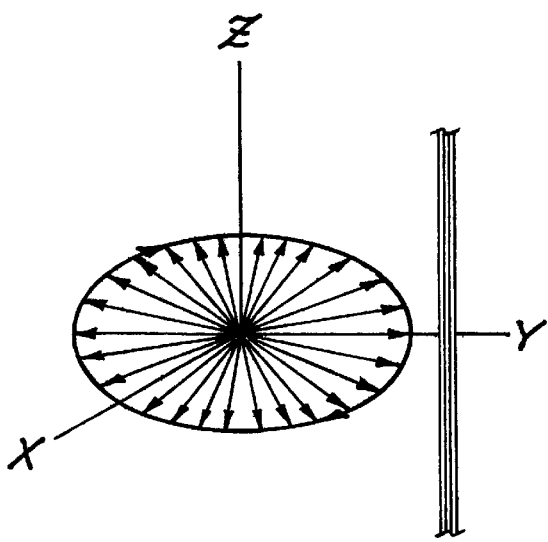

The invention is a method and apparatus for rapidly and accurately determining the fat and oil content of a sample that also contains moisture in amounts that would otherwise preclude NMR determination of the fat and oil content. To aid in the understanding of this invention it may be useful to briefly review the theory behind NMR. A classical, electrodynamic theory of NMR is presented for the reader's edification. Those skilled in the art, however, recognize that other theories of NMR, such as quantum mechanical theory, are also applicable. A detailed discussion of these theories, however, is not necessary to achieve an understanding of the preferred embodiments of the invention.

The nuclei of certain atoms possess a property called "spin." This property is often visualized as a phenomenon similar to a spinning top made of a magnet. In other words, the nuclei of atoms possessing spin also possess an angular momentum and a magnetic moment. For purposes of this discussion the nuclei of a hydrogen atom (e.g., a proton) will serve as an example.

Referring now to FIGS. 1a–1d, when placed in a constant magnetic field C, a proton with a magnetic moment 10 and angular momentum 12 experiences a magnetic torque that forces the proton's magnetic moment 10 to line up parallel to the constant magnetic field C. The proton's magnetic moment also precesses about an axis (Z) parallel to the magnetic field.

If the proton is then exposed to an alternating magnetic field A (such as a RF magnetic field) that is perpendicular to the constant magnetic field C and that oscillates at the same frequency as the rate of precession of the proton (i.e., the Larmor frequency), the proton's magnetic moment 10 tilts away from the direction parallel to the constant magnetic field (i.e., the Z axis). The proton's magnetic moment begins to precess at greater angles 14 like an expanding cone.

With continuing application of the alternating magnetic field A the distal end of the magnetic moment 10 is driven downward until it reaches the X-Y plane. A pulse of alternating magnetic field A at Larmor frequency of sufficient duration to drive the proton's magnetic moment 10 down to the X-Y plane as shown in FIG. 3c is called a 90 degree pulse. In this position the magnetic moment 10 rotates in a circular path creating a sweeping magnetic field that can cut across an electrical conductor 16 positioned nearby thereby inducing an electromagnetic potential or current to flow in the conductor 16. Such a current can be detected which forms the basis for NMR spectroscopy. When the alternating current A is removed the proton's magnetic moment 10 "relaxes" (also referred to as "decay") and eventually returns to its original position. The reorientation and relocation of the magnetic moment is called resonance.

The analytical power of NMR results from the phenomena that both (1) the resonance frequency, and (2) the relaxation time of most nuclei change very slightly—but measurably—depending upon the molecular environment of the nuclei or the nearby chemical bonding. In other words, the NMR response of a particular nuclei is affected by the surrounding atoms and the type of bonding between the atoms. For example and as mentioned previously, the nuclei of liquids (i.e., the hydrogen proton in water) resonates differently than the nuclei in solids. With the proper equipment NMR can even distinguish between and among chemical functional groups. A proton in a methyl group will resonate differently—i.e., have a different chemical shift—than a proton in an ethyl group.

Figure 2:
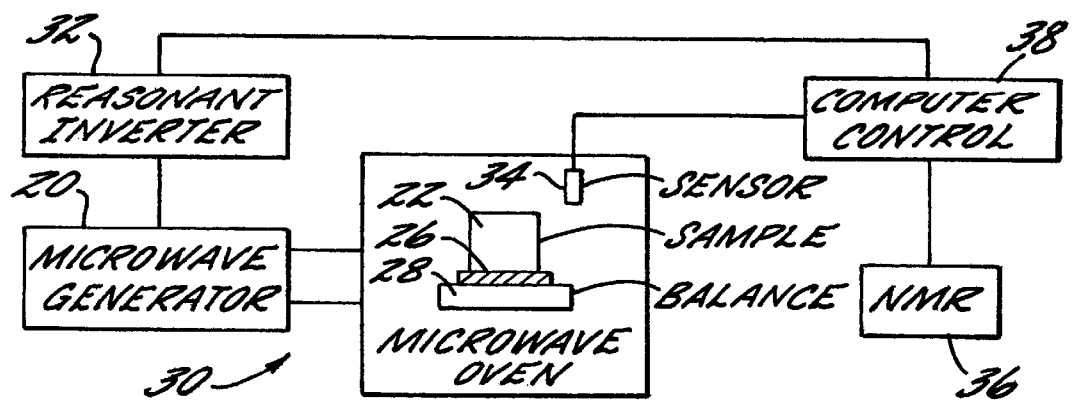
FIG. 2 is a schematic depiction of the apparatus according to the invention.

The invention utilizes both microwave techniques and the NMR phenomenon to determine the moisture content and the fat and oil content of a sample. In particular, the invention is useful to determine the fat and oil content of a sample that also contains moisture (i.e., hydrogen protons in water) in amounts that would otherwise preclude accurate NMR determination of the fat and oil content of the sample. In one embodiment the invention comprises an apparatus for rapidly and accurately determining the moisture fat and oil content of a sample. In broad terms, the invention comprises a device for drying a sample, a carrier or pad for holding the sample and a NMR analyzer for conducting NMR analysis of the sample. In more particular terms and in reference to FIG. 2, the apparatus according to the invention comprises a source of microwave radiation 20 for drying the sample 22 and a cavity 24 in wave communication with the source of microwave radiation 20 for receiving the sample 22 and the sample pad 26. Together, the microwave generator 20 and the cavity 24 form a microwave device, broadly designated at 30. The apparatus also comprises a balance 28 with at least its pan in the cavity 24 for weighing the sample 22 before, during and after drying.

It will be understood that the NMR analysis of the invention can be carried out using either the chemical shift technique, or the pulse and relaxation technique. The former produces a chemical shift spectrum and the latter produces a plot of signal intensity versus time. In order to speak conveniently of either or both, the phrase "NMR response" is used herein. It will also be understood that increasingly better magnets are being developed for NMR devices and other applications. Thus, it is expected that such better magnets will significantly enhance the performance (or alternatively reduce the size, or both) of both types of NMR devices, including their performance in the method and apparatus of this invention.

Suitable microwave devices 30 include any of several microwave devices manufactured by CEM Corporation of Matthews, N.C., such as the SMART SYSTEM 5T™. It will be understood, however, that such devices are exemplary, rather than limiting, of the devices that can be used in accordance with the present invention. Preferably the microwave device 30 is equipped with a sensor 34 for monitoring the temperature of the sample as it is being exposed to microwave radiation. An appropriate technique and apparatus are set forth in copending application Ser. No. 09/156,086, filed Sep. 17, 1998, for "Method and Apparatus for Measuring Volatile Content," the contents of which are incorporated entirely herein by reference. Preferably, the sensor 34 is connected to a control device such as a resonant inverter 32 that is capable of moderating the power output of the microwave source to maintain a constant temperature during the drying process. An apparatus with such capability is described in U.S. patent applications Ser. No. 09/063,545, filed Apr. 21, 1998, and Ser. No. 09/343,349, filed Jun. 30, 1999, both for "Continuously Variable Power for Microwave Assisted Chemistry," which are commonly assigned with this application to CEM Corporation of Matthews, N.C., and whose contents are incorporated herein by reference in their entirety.

The NMR device preferably comprises a pulsed NMR device; i.e., one that measures the relaxation times of protons following an RF pulse rather than their chemical shift (resonance), and then provides a plot of signal intensity versus time. The detailed theory and operation of pulsed NMR and the use of Fourier Transform to present the relevant information in useful form is generally well understood in the art, and thus the discussions herein will tend to relate to the invention rather than to these underlying and well-understood concepts and practices. Appropriate pulsed NMR devices are, however, available from a number of commercial sources including, but not limited to Oxford Industries plc, Oxford, UK.

It will be understood that as used herein, the phrase "identify the relaxation times of protons" also refers to any appropriate interpretation of this data, including but not limited to, the use of Fourier Transform to produce a plot of signal intensity versus relaxation time, which in turn provides the desired information about fat content.

The sample pad 26 utilized in the apparatus according to the invention is specifically designed for use in the claimed NMR analysis method. As mentioned previously, current methods for fat and oil determination using NMR analysis tend to be less reliable measurements by losing a percentage of fat and oil due to run off during melting. The claimed invention eliminates or reduces this uncertainty by incorporating a sample pad that may be directly transferred from the microwave drying device to the NMR analyzer and that conserves the entire sample for NMR analysis.

The sample pad 26 is substantially transparent to microwave radiation and is free of atoms that would interfere with or mask the NMR response of the protons in the fats and oils in the sample. The characterization, "free of atoms that would . . . interfere or mask . . . fat and oils," as used throughout this specification should be understood to mean that the sample pad is not devoid of all atoms that could interfere with NMR measurement. This characterization means that the article, in this case the sample pad, contains such atoms in such low quantity that their effect on the NMR analysis is statistically insignificant. Preferably the pad is of low mass, porous, hydrophilic, and lipophilic. The porosity along with the hydrophilic nature of the pad retains any liquid present in the original sample that may drain off prior to drying the sample thus enabling accurate weight measurement of the original sample. The porosity along with the lipophilic nature of the pad ensures that any fat or oil melted during the drying of the sample is retained in the sample pad thus enabling an accurate weight measurement after the drying of the sample. The sample pad must also be of a size and pliable enough for insertion into the analyzing chamber of the NMR analyzer. Suitable materials for use in forming the sample pad include quartz fibers or glass fibers, the use of which in microwave techniques is set forth in an analogous manner, for example, in U.S. Pat. No. 5,378,878, which is commonly assigned herewith and incorporated entirely herein by reference.

The apparatus according to the invention also preferably comprises a sheet material that is nonporous with respect to oils, melted fats, and other liquids, and that is free of atoms that would interfere with or mask the NMR response of the protons in the fats and oils in the sample. This material is wrapped around the sample and sample pad during the NMR analysis. The sheet material aids in maintaining the integrity of the sample during NMR analysis. Polytetrafluoroethylene polymers (PTFE), Teflon, or other similar materials possessing the above-described characteristics are suitable for use as the sheet material. PTFE sheeting is commercially available, for example, under the "e-com plastics" trade name from Rideout Plastics Company, Inc., of San Diego, Calif.

The apparatus according to the invention also comprises a NMR analyzer 36 and a processor 38 for quantitatively assessing the moisture and fat content of the original sample. Furthermore, for many food products, the remainder of the sample (i.e., the portion other than water, oil, or fat) will be known to be almost entirely protein (meats, fish, dairy products) or entirely carbohydrate (fruits and vegetables). Accordingly, the measured weight of the initial sample, when combined with the results of moisture content and fat and oil content, can be used to determine the absolute and percentage amount of protein or carbohydrate in the original sample.

The processor of the invention can be any appropriate device that can calculate moisture content based on weight loss, and fat and oil content based on the original weight and the amount of fat and oil as determined by the NMR analyzer. Thus, the processor 38 preferably collects data from both the microwave device 30 and the NMR processor 38, and uses it to calculate the moisture and fat and oil content of samples. For most purposes, a processor the same as or similar to those in a personal computer are quite satisfactory when combined with the appropriate software. The PENTIUM® class of processors (e.g., Pentium, Pentium II, and Pentium III) from Intel, and the CELERON® class from AMD are exemplary, but not limiting, of suitable processors. Because such processors and the types of software used to calculate the desired results are well understood in the art and widely available, they will not be otherwise discussed in detail herein.

As noted above, the NMR analyzer utilized in the apparatus according to the invention may be of any of several types of NMR analyzers commercially available from NMR vendors provided that they can measure the fat and oil content of the desired category of samples.

The apparatus according to the invention is preferably oriented such that the components of the apparatus are suitable situated proximate one another to minimize the time needed to transfer the sample from the drying device to the NMR analyzer. Minimizing the transfer time also minimizes any heat loss in the sample which may occur while moving the sample between the microwave device 30 and the NMR analyzer 36. This aspect of the method is discussed in more detail below.

A further embodiment of the invention encompasses a method of rapidly and accurately determining the fat and oil content of a sample that also contains moisture in amounts that would otherwise preclude NMR determination of the fat and oil content of the sample. This embodiment of the invention comprises the steps of weighing the sample, drying the sample by subjecting the sample to electromagnetic radiation in the microwave frequencies, transferring the entire sample to an NMR analyzer, measuring the NMR response of the sample to identify the characteristics that are associated with fats and oils, and comparing the NMR response of the sample with NMR data from similar samples of known fat and oil content to determine the fat and oil content in the sample.

Weighing the sample prior to drying is necessary for a final determination of the content of the sample. Without an initial weight, determining the weight percentage of individual components is difficult. Preferably the sample 22 is weighed while positioned on a sample pad 26 of known weight. The sample pad 26 is preferably of the type previously discussed. The sample and sample pad may be weighed prior to the drying step on a stand-alone balance. Preferably the sample and sample pad are placed on a balance 28 in the cavity 24 that is part of the microwave device 30. Most typically, only the pan of the balance extends into the cavity. The balance is preferably connected to (i.e., in input and output communication with) a processor that is capable of electronically recording the weight of the sample and sample pad. Placing the balance 28 within the cavity 24 also allows for continuous monitoring of any weight change that occurs by virtue of driving off moisture during the drying step. Finally, placing the balance 28 in the cavity 24 provides an avenue for obtaining a final post-drying weight measurement without having to disturb the sample thereby increasing the efficiency of the process and eliminating a possible source of data corruption. The weight change observed and recorded during the drying step provides the data necessary for calculating the quantity and weight percentage of moisture in the original sample. This weight change also provides data necessary to determine the weight percentage of fat and oil in the sample, given that the NMR response is usually representative of the gross amount of fat and oil, rather than a proportional or percentage amount.

Those skilled in the art recognize that the term "dry" is a relative term. The term "dry" or "dried" as used herein means the point at which the moisture in a sample is reduced to a level where it will not mask or otherwise interfere with the fat and oil spectra measured by the NMR analyzer. This level of "dryness" is statistically determinable using appropriate statistical analysis and experimental data readily available to those skilled in the art.

The actual drying of the sample is accomplished by exposing the sample 22 and the sample pad 26 to electromagnetic radiation in the microwave frequencies. As well understood by those familiar with the electromagnetic spectrum, the term "microwave" is often used generically to refer to radiation with wavelengths of between about 1000 and 500,000 microns ($\mu$), and corresponding frequencies of between about $1\times10^9$ and $5\times10^{11}$ Hertz (Hz). These are arbitrary boundaries, however, and other sources refer to microwaves as having frequencies of between about $10^8$ Hz and $10^{12}$ Hz and wavelengths of between about 300 centimeters (cm) and 0.3 millimeters (mm). For commercial and consumer purposes in the United States, the available microwave frequencies are regulated by the Federal Communications Commission and are generally limited to certain frequencies such as 2450 megahertz (MHz).

In contrast to some conventional heating techniques in which a vessel is heated externally in order to in turn heat the reagents inside, microwave radiation heats the reagents directly and can be carried out—and indeed is desirably carried out—in vessels that are unaffected by microwave energy, such as the previously discussed sample pad. Thus, microwave radiation tends to heat chemical samples very quickly and to high temperatures unless the radiation is somehow moderated. Accordingly, the method according to the invention preferably comprises moderating the drying of the sample by moderating the microwave radiation utilized to heat the sample. As discussed previously, this may be accomplished using techniques and apparatus discussed in the patents and applications previously incorporated herein, or by any other technique that provides the appropriate information and control. Moderating or otherwise controlling the microwave radiation also provides the benefit of keeping the sample at a substantially constant temperature during the drying process. Achieving a constant temperature during the drying process provides a setpoint for conducting the NMR analysis which is preferably conducted at a temperature that matches or closely matches the temperature of the drying step. It has been determined in accordance with the invention that uniformity of temperature between the drying step and the NMR analysis improves the accuracy of the method, particularly for repeated or consecutive samples of the same or similar materials.

During the drying step, the sample and sample pad are preferably heated until at least a portion, preferably a large portion, and most preferably all of the fat and oil in the sample are completely melted. Melting the fat and oil necessarily means that some of the fat and oil will drain from the sample. The lipophilic sample pad collects or absorbs any fat and oil that drains from the sample thereby preserving the fat and oil content in the sample for later NMR analysis, and thereby enhancing the accuracy of the results.

After the sample is sufficiently dry and the fat and oil are melted and the necessary weight measurements are taken, the entire sample and sample pad are rapidly transferred to the NMR analyzer 36. In a preferred embodiment the sample 22 and sample pad 26 are wrapped in a sheet material prior to being placed in the NMR analyzer. Wrapping the sample and sample pad in the sheet material aids in preserving the integrity of the sample as it is being transferred to the NMR analyzer. The sheet material should be nonporous to oils, melted fats, and other liquids, and free of atoms that would interfere with or mask the NMR response of the protons in the fats and oils of the sample. As mentioned previously, PTFE is a suitable material for this purpose. It will be understood that the term "wrapped" is not a limitation on the claimed invention, and that any physical technique that captures the entire sample and entire pad (and thus all of the fats and oils) in a manner suitable for the NMR analysis step can be used.

After the sample and sample pad are wrapped in the sheet material the sample and sample pad are subjected to NMR analysis, preferably at substantially the same temperature as the drying step, the NMR analysis generates the NMR response data for the components of the sample.

The NMR data from of the sample may then be fed to a processing unit where it may be mathematically manipulated using calculations well known in the NMR art to quantitatively determine the quantity of fat and oil in the sample. Alternatively, the NMR response of the sample may be compared to NMR data for samples of known fat and oil content to determine the quantity of fat and oil in the sample. When the comparison method is utilized, the method of the invention can also comprise the step of generating a plurality of NMR spectra of samples of known fat and oil content. The comparison spectra can also be gathered after the sample is analyzed, but this tends to increase the amount of time necessary to conduct the overall analysis.

The use of known NMR response data from known samples is generally most appropriate for analyses in which samples of the same material are tested for quality control or other similar purposes. Stated differently, and using foodstuffs as the example, samples of a particular meat product will almost always have a moisture/fat/oil protein content that falls within an expected profile. As a result, the number of known NMR data sets required for matching or comparison purpose will be quite reasonable, and in some cases, even rather small.

In yet a further embodiment, the invention comprises a sample for NMR measurement. The sample comprises an organic portion containing at least some fats and oils. The organic portion is situated on a sample pad that is substantially transparent to microwave radiation and is free of atoms that would interfere with or mask the NMR response of the protons in the fats and oils in the sample. The sample and sample pad are secured by wrapping them in the sheet material describer earlier herein that is free of atoms that would interfere with or mask the NMR response of the protons in the fats and oils in the sample.

Figure 3:
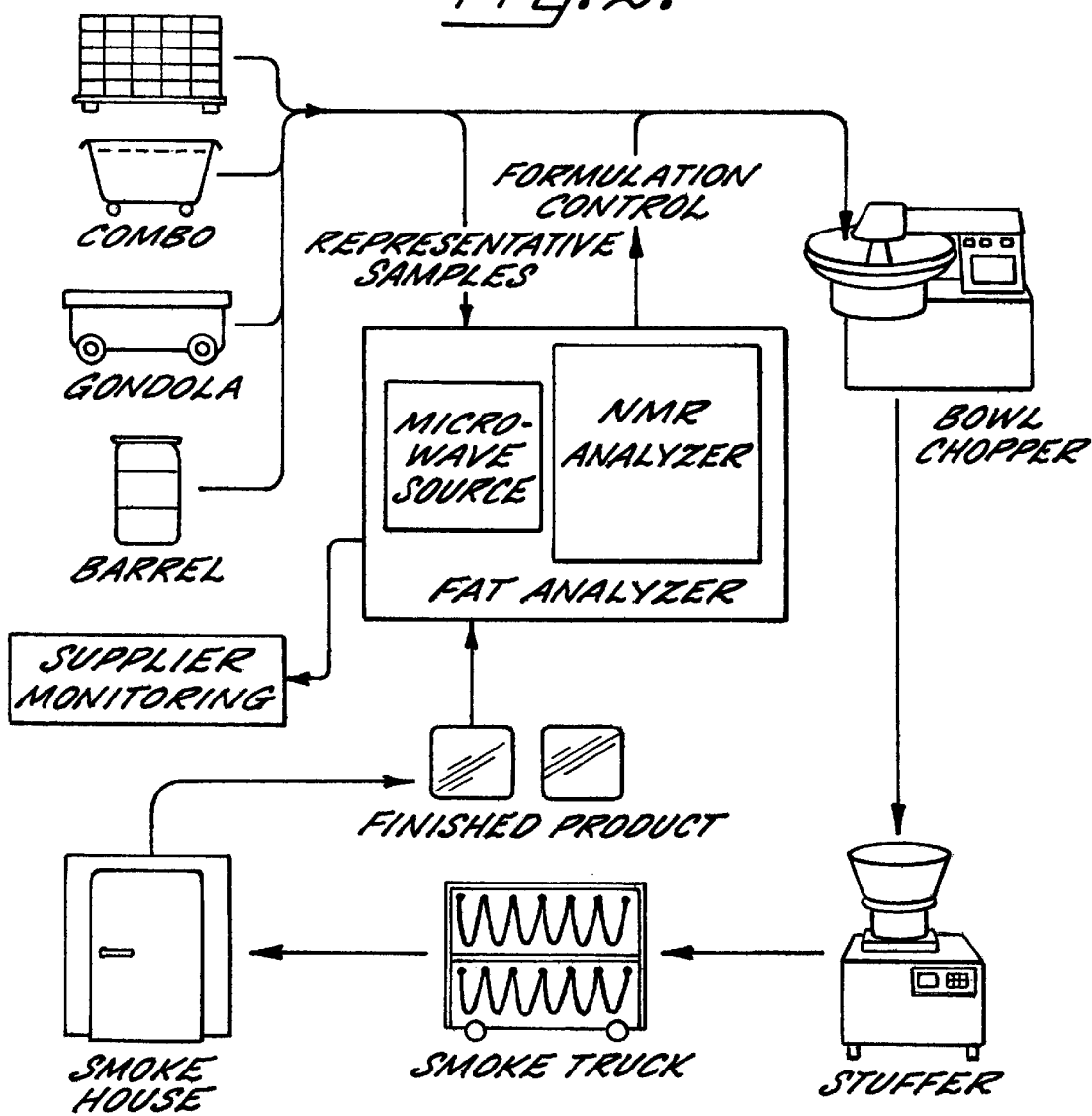
FIG. 3 is a flow chart representing one implementation of the invention.

FIG. 3 is a flow chart illustrating one manner in which the claimed invention can be integrated within and improves current production processes. In particular, FIG. 3 relates to the production of stuffed meat products such as hot dogs or sausages. Raw material is provided to the process via pallets, barrels, gondolas, or other usual means. The raw material is then sampled to determine the fat and oil content of the material. Based upon the calculated fat and oil content in the raw material the formulation of the product may be adjusted to bring the percentage of fat and oil content within acceptable levels. This information may also be shared with the raw material suppliers to aid them in preparing suitable raw material for future use. As FIG. 3 further illustrates, the finished product can be tested in a manner identical to the raw material.

Figure 6:
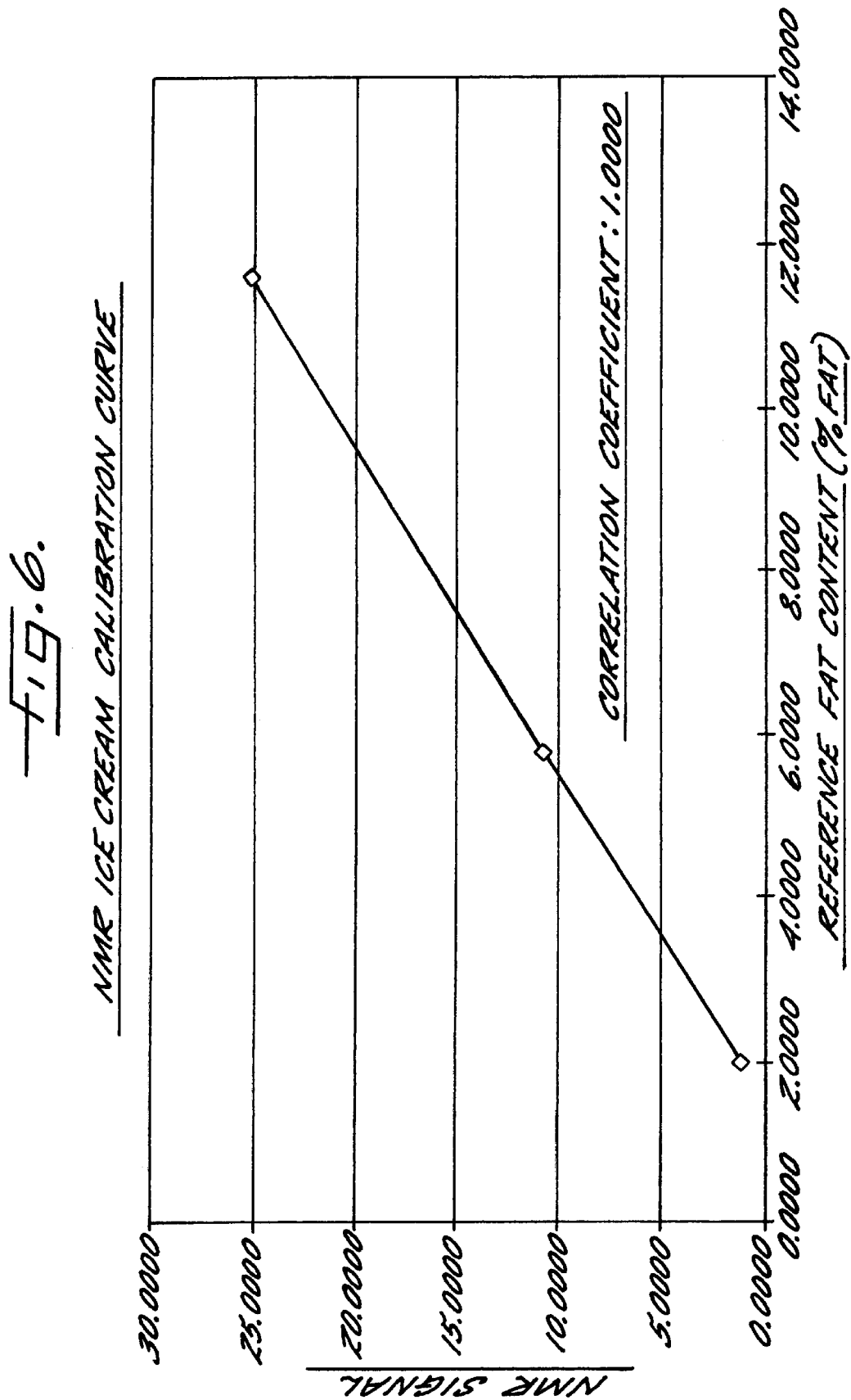
FIGS. 6 and 7 are calibration curves according to the present invention.
Figure 7:
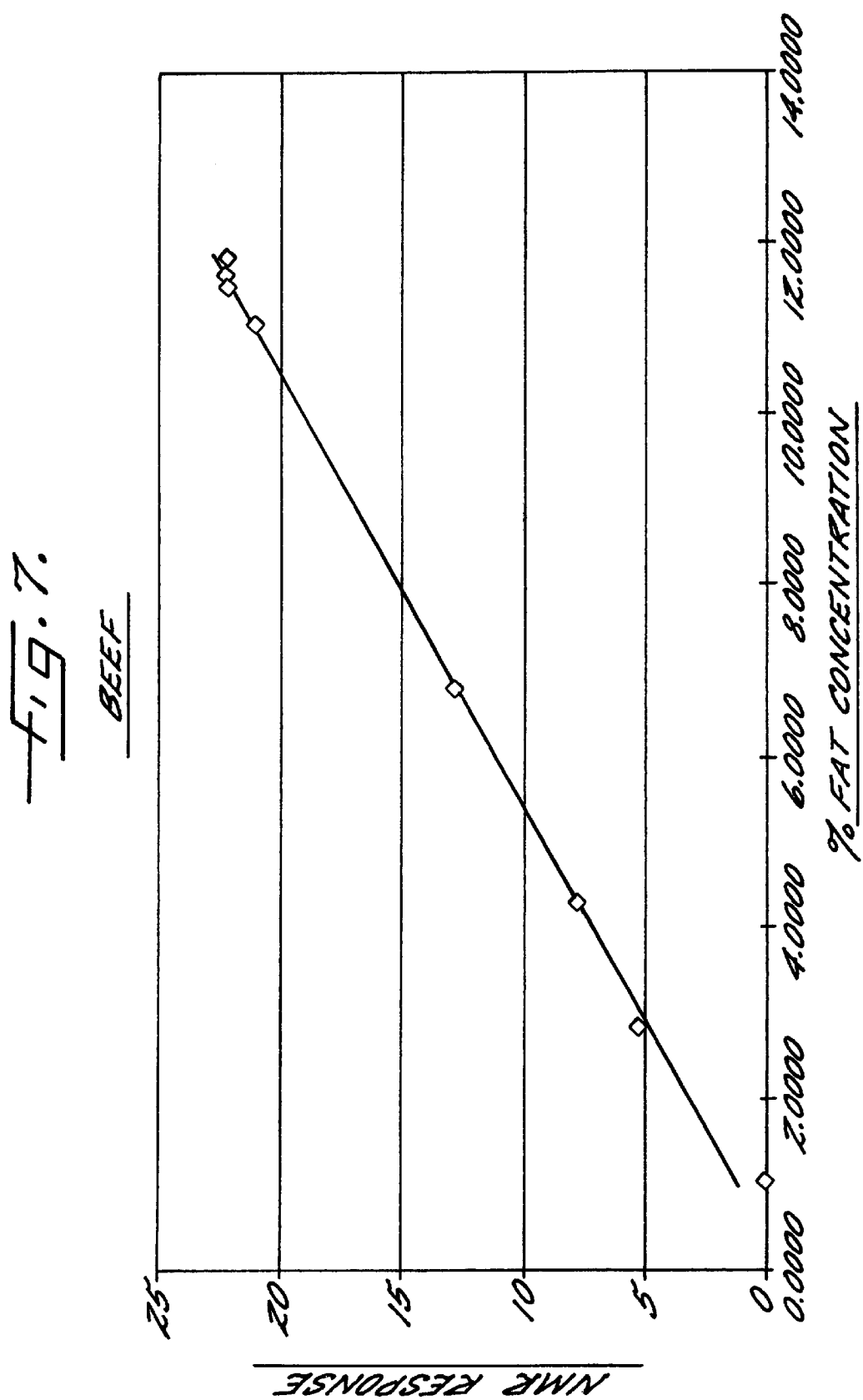

FIGS. 6 and 7 are calibration curves for several types of food samples, and illustrate the manner in which the NMR analyzer is calibrated against known samples.

Following calibration, the following results were obtained when the calibrated device was used to analyze the respective samples:

| Sample Wt. (g) | Fat Content (%) Standard Method | Fat Content (%) Microwave NMR Method |
|---|---|---|
| Ice Cream: | | |
| 1.6750 | 2.00 | 2.00 |
| 1.3240 | 5.80 | 5.80 |
| 1.3240 | 5.80 | 5.82 |
| 1.6630 | 11.59 | 11.59 |
| Beef: | | |
| 3.4340 | 7.66 | 7.64 |
| 5.0730 | 12.83 | 12.57 |
| 3.6670 | 21.00 | 21.05 |
| 4.5930 | 22.18 | 21.94 |
| 3.7430 | 22.29 | 22.61 |
| 4.1210 | 22.30 | 22.61 |
| 3.8900 | 22.30 | 22.11 |
| 6.6770 | 9.01 | 8.91 |
| 5.0640 | 14.23 | 14.38 |
| 5.2030 | 23.58 | 23.53 |
| Cheddar Cheese: | | |
| 1.7070 | 5.53 | 5.57 |
| 1.5250 | 21.16 | 21.07 |
| 1.6270 | 33.12 | 33.17 |
| Sour Cream: | | |
| 3.0950 | 1.52 | 1.47 |
| 3.8400 | 1.52 | 1.44 |
| 3.7280 | 11.72 | 12.05 |
| 4.2020 | 17.48 | 17.27 |

As these results indicate, the fat content of these samples measured according to the invention correlates almost perfectly with the actual fat content of these samples.

After the proper formulation is prepared the finished product (e.g., hot dog) is tested to confirm that fat and oil content remains within acceptable levels. The claimed invention allows for the rapid analysis of multiple samples thereby allowing the production process to operate at maximum efficiency.

Because the method begins with the step of weighing the sample, the percentages of fats, oil, and moisture can be calculated quickly and directly.

Figure 4:
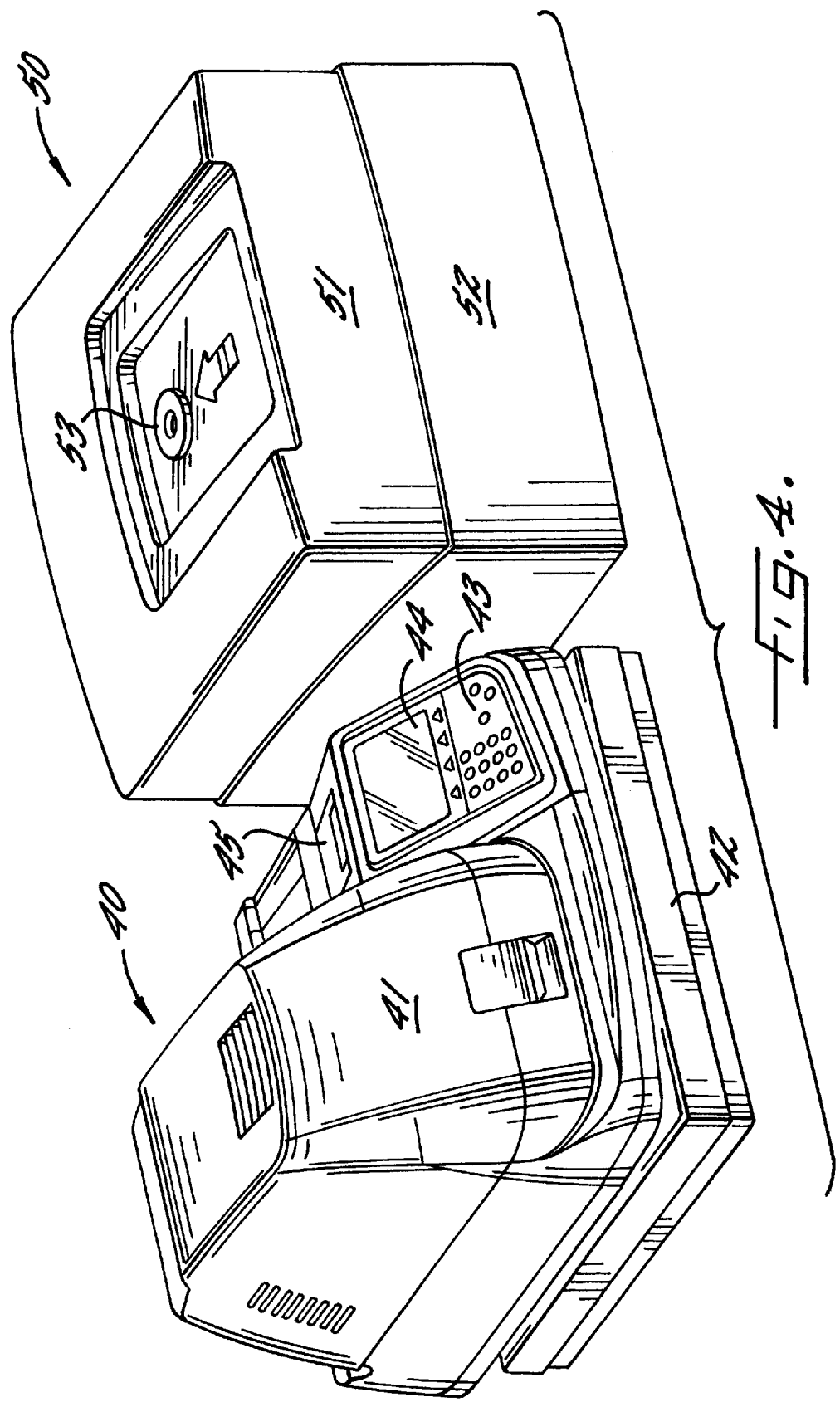
FIGS. 4 and 5 are perspective views of one embodiment of the apparatus according to the present invention.
Figure 5:
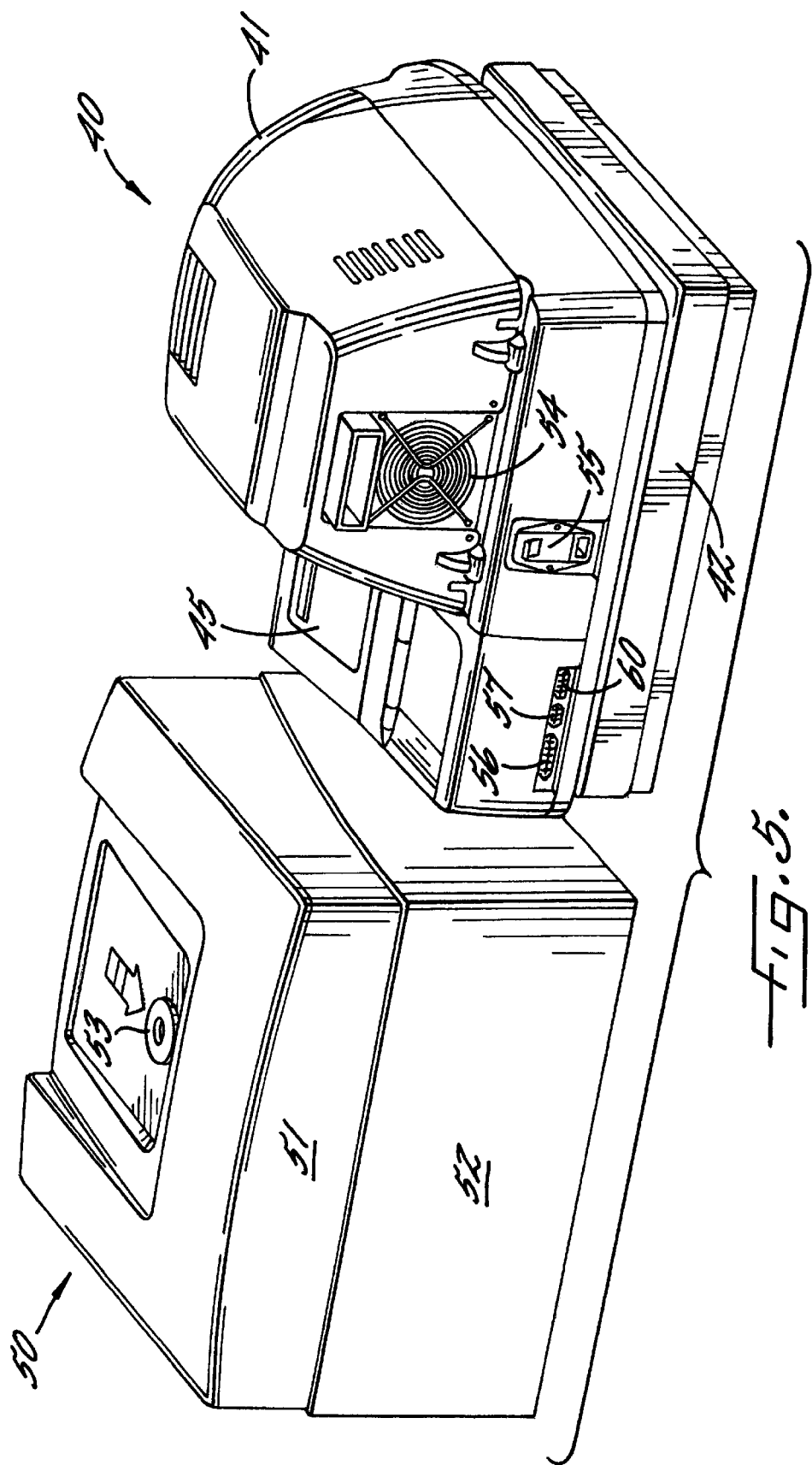

FIGS. 4 and 5 are respective front and rear perspective views of an apparatus according to the present invention. In FIG. 4, the microwave device is broadly designated at 40, and the NMR analyzer is broadly designated at 50. The microwave device 40 can be any suitable device that includes an appropriate cavity, source of microwave radiation, and balance, but in preferred embodiments is the device disclosed and described in co-pending and commonly assigned application Ser. No. 09/398,129 filed Sep. 17, 1999 for "High Efficiency Cavity Design and Moisture Analyzer," the contents of which are incorporated entirely herein by reference. The device 40 includes a microwave cavity (not shown) that is underneath the cover portion 41 of the analyzer 40. The microwave source is preferably either a magnetron or a resonant inverter. The microwave device 40 further includes a balance, portions of which are included in the lower housing 42 illustrated in FIG. 4. FIG. 4 also illustrates the control pad 43 and display 44 for an appropriate microprocessor as described earlier herein. The microwave device 40 illustrated in FIG. 4 also includes a small tape printer 45 for producing the results on paper as well as on the display 44.

As noted earlier herein, the NMR device 50 is preferably a device available from Oxford Industries plc, Oxford, UK. The NMR device 50 includes a housing formed of upper portions 51 and 52 respectively. An appropriate sample holder 53 is positioned in the upper housing 51 for holding a sample therein. Although, the detailed operation of NMR devices of this type are well known, and will not be described in detail herein, the device 50 will include a magnet that produces a static magnetic field, as well as a source of an oscillating electromagnetic field that provides the RF field that in turn engages the protons and then measures their relaxation times in the manner previously described.

FIG. 5 illustrates the rear portion of the respective devices 40 and 50. FIG. 5 illustrates that the microwave device 40 includes an appropriate fan 54, a power switch 55, and respective output ports 56, 57 and 60, for connecting the device 40 with other appropriate devices, typically PC or Macintosh-based computers that can carry out additional calculations based on the data obtained, if such are desired or necessary beyond those produced by the processor of the device 40.

In another aspect, the invention comprises a wrapper for an NMR sample. FIG. 8 illustrates the wrapper 62, which is formed of a sheet material that is free of atoms that would interfere with or mask the NMR response of the protons in fats and oils. Because the method of the invention uses microwave techniques to dry the samples, and because the samples are typically placed between two sample pads in the microwave device (e.g., pads 63 in FIG. 8), the sheet 62 has an area large enough to completely wrap a food sample 59, or both a food sample and the pads 63, while small enough to fit within the sample field portion of an NMR analyzer when the sheet 62 is wrapped around a sample, or preferably around both the sample and the pads 63. Preferably, the wrapped pads and sample, shown schematically at 64 in FIG. 9, are folded and placed in an appropriate holder 65 (FIG. 10) before being placed in the NMR analyzer 50 (FIGS. 4 and 5). The holder 65 is typically cylindrical in shape, and likewise formed of a material that does not mask, or otherwise interfere with, the NMR response of the sample. Appropriate materials for NMR use are well known to those of ordinary skill in this art and can be selected as desired or necessary without undue experimentation.

The sheet 62 is preferably formed of a fluorocarbon material, most typically polytetrafluoroethylene (PTFE). Preferably, the sheet 62 is somewhat larger than the pad it is used to wrap, but usually not more than about two-and-a-half times larger in area. Typical microwave sample pads usually measure several inches in length and width (e.g., 4 by 5 inches) and so the sheet material 62 is preferably slightly larger.

The invention has been described in detail, with reference to certain preferred embodiments, in order to enable the reader to practice the invention without undue experimentation. However, a person having ordinary skill in the art will readily recognize that many of the components and parameters may be varied or modified to a certain extent without departing from the scope and spirit of the invention. Furthermore, titles, headings, or the like are provided to enhance the reader's comprehension of this document and should not be read as limiting the scope of the present invention. Accordingly, only the following claims and reasonable extensions and equivalents define the intellectual property rights to the invention.

That which is claimed is:

1. A sample for NMR measurement comprising:
    an organic portion containing at least some fats and oils;
    a pad that is heat resistant, lipophilic and substantially transparent to microwave radiation and is free of hydrogen atoms that would interfere with or mask the NMR response of the protons in the fats and oils in the sample;
    a pliable sheet material that is free of hydrogen atoms that would interfere with or mask the NMR response of the protons in the fats and oils in the sample, and that is substantially nonporous to oils, melted fats, and other liquids, and strong enough to withstand being wrapped and folded into a size that fits within, the sample field of an NMR analyzer; and
    said sheet material being wrapped around said organic portion and said pad.

2. A sample according to claim 1 at a temperature at which the fats and oils are partially melted.

3. A sample according to claim 1 wherein said organic portion is on said pad, and said pad and said organic portion are wrapped in said sheet material.

4. A sample according to claim 1 wherein said pad is hydrophilic.

5. A sample according to claim 1 wherein said pliable sheet material comprises a fluorocarbon polymer.

6. A sample according to claim 5 wherein said pliable sheet material comprises polytetrafluoroethylene.

7. A sample according to claim 1 wherein said pad comprises glass fibers.

8. A sample according to claim 1 wherein said pad comprises quartz fibers.

* * * * *

UNITED STATES PATENT AND TRADEMARK OFFICE
CERTIFICATE OF CORRECTION

PATENT NO.    : 6,548,304 B2
DATED         : April 15, 2003
INVENTOR(S)   : Collins et al.

It is certified that error appears in the above-identified patent and that said Letters Patent is hereby corrected as shown below:

<u>Title page,</u>
Item [75], add
-- Edward E. King, Charlotte, NC (US) --.

Signed and Sealed this

Eighteenth Day of November, 2003

JAMES E. ROGAN
*Director of the United States Patent and Trademark Office*